(12) United States Patent
Feldman (10) Patent No.: US 12,369,798 B2
(45) Date of Patent: Jul. 29, 2025

(54) OPTOACOUSTIC LASER ASSEMBLY WITH DUAL OUTPUT FROM A SINGLE CAVITY LASER

(71) Applicant: Seno Medical Instruments, Inc., San Antonio, TX (US)

(72) Inventor: Samuel Henry Feldman, San Antonio, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 973 days.

(21) Appl. No.: 17/410,507

(22) Filed: Aug. 24, 2021

(65) Prior Publication Data
US 2022/0071493 A1    Mar. 10, 2022

Related U.S. Application Data

(60) Provisional application No. 63/075,910, filed on Sep. 9, 2020.

(51) Int. Cl.
| | |
|---|---|
| A61B 5/00 | (2006.01) |
| H01S 3/10 | (2006.01) |
| H01S 3/107 | (2006.01) |
| H01S 3/108 | (2006.01) |
| H01S 3/16 | (2006.01) |

(52) U.S. Cl.
CPC ........ *A61B 5/0095* (2013.01); *H01S 3/10061* (2013.01); *H01S 3/107* (2013.01); *H01S 3/1083* (2013.01); *H01S 3/1611* (2013.01); *H01S 3/1643* (2013.01)

(58) Field of Classification Search
CPC ... A61B 5/0095; H01S 3/10061; H01S 3/107; H01S 3/1083; H01S 3/1643; H01S 3/1611
See application file for complete search history.

(56) References Cited

U.S. PATENT DOCUMENTS

| | | | |
|---|---|---|---|
| 2013/0122564 A1* | 5/2013 | Kimmel | C12M 35/04 435/283.1 |
| 2013/0281819 A1* | 10/2013 | Schmid | A61B 5/14542 600/407 |
| 2019/0343437 A1* | 11/2019 | Ray | A61B 5/02055 |
| 2021/0260401 A1* | 8/2021 | Thorhauge | G02F 1/3534 |

* cited by examiner

*Primary Examiner* — Gerald Johnson
(74) *Attorney, Agent, or Firm* — Josef L. Hoffmann; The Small Patent Law Group LLC (57) ABSTRACT

A laser assembly is provided that includes a laser pump chamber that emits a first light through a laser cavity at a first wavelength, and a polarization assembly that receives the first light and converts the first light into a pulsed light that includes the first light at the first wavelength and a first polarization. The laser assembly also includes a second light at the first wavelength and a second polarization.

20 Claims, 4 Drawing Sheets

OPTOACOUSTIC LASER ASSEMBLY WITH DUAL OUTPUT FROM A SINGLE CAVITY LASER

CROSS-REFERENCE TO RELATED APPLICATIONS

This application claims priority to U.S. Provisional Application No. 63/075,910 entitled Optoacoustic Laser Assembly With Dual Output From A Single Cavity Laser filed Sep. 9, 2020, hereby incorporated by reference in its entirety.

TECHNICAL FIELD

The present invention relates in general to the field of medical imaging, and in particular to a system relating to an optoacoustic laser

BACKGROUND

Optoacoustic imaging systems visualize thin tissue slices noninvasively through skin at a tissue site. A tissue site may contain a variety of tissue structures that may include, for example, tumors, blood vessels, tissue layers, and components of blood. In optoacoustic imaging systems, light is used to deliver optical energy to a planer slice of the tissue site, which as a result of optical absorption with the tissue structures, produce acoustic waves. An image spatially representing the tissue site can be generated by performing image reconstruction on acoustic signals that return to an ultrasound transducer array.

A laser light source typically provides the optical energy required to generate the acoustic waves. The laser light source often utilizes two separate lasers, with two laser resonators generating light at different wavelengths. The laser pumps may also be blanked, impeded, etc. in order to provide a pulsed light output.

BRIEF SUMMARY

New and useful systems, apparatuses, and methods for providing optoacoustic imaging are set forth in the appended claims. Illustrative embodiments are also provided to enable a person skilled in the art to make use of the claimed subject matter.

Objectives, advantages, and a preferred mode of making and using the claimed subject matter may be understood best by reference to the accompanying drawings in conjunction with the following detailed description of illustrative embodiments.

In accordance with embodiments herein, a laser assembly is provided that includes a laser pump chamber that emits a first light through a laser cavity at a first wavelength, and a polarization assembly that receives the first light and converts the first light into a pulsed light that includes the first light at the first wavelength and a first polarization. The laser assembly also includes a second light at the first wavelength and a second polarization.

Optionally, the polarization assembly includes a polarizing beam splitter that converts the first light into the first light at the first wavelength and first polarization, and the second light at the first wavelength and the second polarization. In one aspect, the polarization assembly includes a first Pockels cell and a first reflective component that reflects the first light and a second Pockels cell and a second reflective component that reflects the second light. In another aspect the polarization assembly includes a first waveplate and a second waveplate.

Optionally, the laser cavity is the only cavity of the laser that emits the first light. In one aspect, the laser assembly also includes an optical parametric oscillator that converts the pulsed light at the first wavelength into a first converted light at a second wavelength and a second converted light at a third wavelength. In one aspect, the first wavelength, second wavelength, and third wavelength are different wavelengths. In another aspect, the pulsed light pulses in a range between 50 microseconds and 400 microseconds.

In one or more embodiments, an optoacoustic probe is provided for optoacoustic imaging of a volume. The optoacoustic probe has a distal end operable to contact the volume and a proximal end. The optoacoustic probe includes a laser assembly configured to generate a pulsed light that includes a first light at a first wavelength and a first polarization, and a second light at the first wavelength and a second polarization along a light path to generate optoacoustic return signals when the light reacts with the volume, and a transducer assembly including a transducer configured to receive the optoacoustic return signals and an acoustic lens provided over the transducer.

Optionally, the laser assembly includes a polarizing beam splitter that receives light from a laser pump chamber and converts the light into the first light at the first wavelength and the first polarization and the second light at the first wavelength and the second polarization. In one aspect the laser assembly includes a first Pockels cell and first reflective component that reflects the first light back to the polarizing beam splitter, and a second Pockels cell and second reflective component that reflects the second light back to the polarizing beam splitter. In another aspect, the laser assembly pump chamber has only one cavity. In one example, the laser assembly pump chamber is made from only Nd:YAG based material. In another example, the light is not emitted by a laser chamber pump having an Alexandrite based material. In one embodiment, the laser assembly includes an optical parametric oscillator that converts the pulsed light into a first converted light at a second wavelength and a second converted light at a third wavelength. In another embodiment, the pulsed light is pulsed in a range of between 50 microseconds and 400 microseconds between pulses.

In one or more embodiments an optoacoustic probe is provided for optoacoustic imaging of a volume. The optoacoustic probe has a distal end operable to contact the volume and a proximal end. The optoacoustic probe includes a laser assembly configured to generate a pulsed light at less than 200 microseconds between pulses along a light path to generate optoacoustic return signals when the light reacts with the volume, and a transducer assembly including a transducer configured to receive the optoacoustic return signals and an acoustic lens provided over the transducer.

Optionally, the laser assembly includes a laser pump chamber that emits a first light at a first wavelength, and a polarizing beam splitter that converts the first light into a first converted light with a first polarization, and a second converted light at a second opposite polarization. In one aspect, the laser pump chamber is made from only Nd:YAG based material. In another aspect, the laser assembly only has a single laser pump chamber.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Embodiments herein may be implemented in connection with one or more of the systems and methods described in one or more of the following patents, publications, and/or published applications, all of which are expressly incorporated herein by reference in their entireties:

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015

U.S. Publication 2016/0187481, titled "Opto-Acoustic Imaging System With Detection Of Relative Orientation Of Light Source And Acoustic Receiver Using Acoustic Waves" filed Oct. 30, 2015.

As used herein the term "light" shall refer to any and all electromagnetic radiation, including but not limited to UV radiation, visible light, infrared radiation, etc. Light as used herein is in no way limited to the visible spectrum. Light may include characteristics including polarization, wavelength, frequency, etc. When a characteristic of light is changed, enhanced, diminished, altered, etc. the light may be considered converted, changed, enhanced, diminished, altered, etc.

A laser assembly is provided with a laser pump that provides pulsed light from a first light and second light that have the same wavelength and frequency, but different polarization. The laser assembly utilizes a polarizing beam splitter along with first and second Pockels cells to form the pulsed light and deliver the pulsed light back through a laser pump cavity. The pulsed light is then converted as needed by an optical parametric oscillator cavity to provide desired wavelengths and frequencies for an optoacoustic probe.

Figure 1:
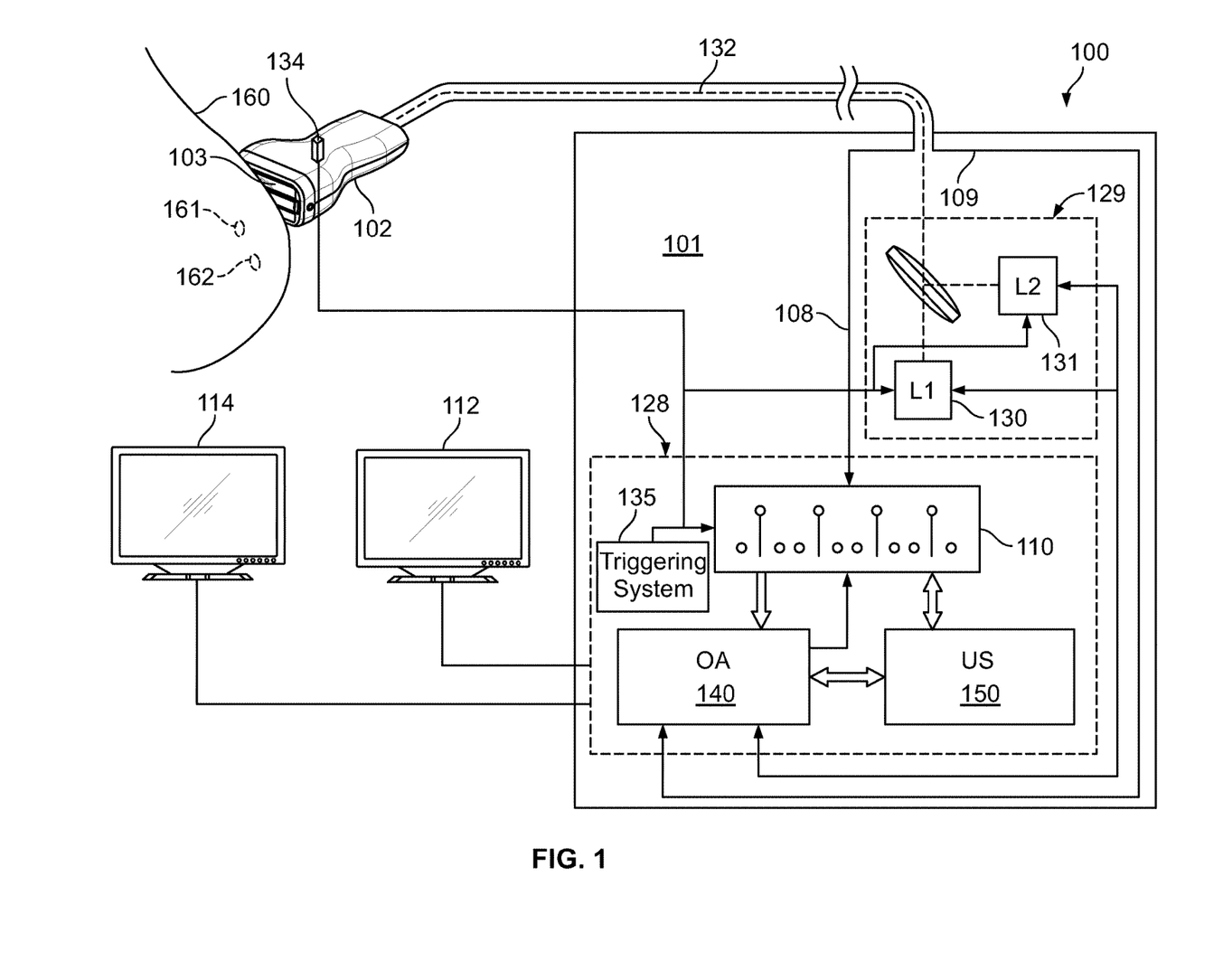
FIG. 1 shows a schematic block diagram illustrating an embodiment of a combined optoacoustic and ultrasound system that may be used as a platform for the methods and devices disclosed herein.

Turning to FIG. 1, generally, device 100 provides an optoacoustic system that may also be employed as multimodality, combined optoacoustic and ultrasound system. In an embodiment, the device 100 includes a probe 102 connected via a light path 132 and an electrical path 108 to a system chassis 101. Within the system chassis 101 is housed a laser assembly 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, a triggering system 135, an optoacoustic processing and overlay system 140 and an ultrasound instrument 150. In one embodiment, the triggering system 135 is configured to actuate and control operation of laser pump chamber 130. The laser pump chamber 130 is utilized in creating signals for imaging purposes as will be described in greater detail with reference to FIGS. 3-4. In an embodiment, the laser assembly 129 is capable of producing pulses of light of at least two different polarizations and wavelengths. The output of the laser pump chamber 130 of the laser assembly 129 is delivered to the probe 102 via the light path 132.

One or more displays 112, 114, which may be touch screen displays, are provided for displaying images and all or portions of the device 100 user interface. One or more other user input devices (not shown) such as a keyboard, mouse, and various other input devices (e.g., dials and switches) may be provided for receiving input from an operator.

Figure 2:
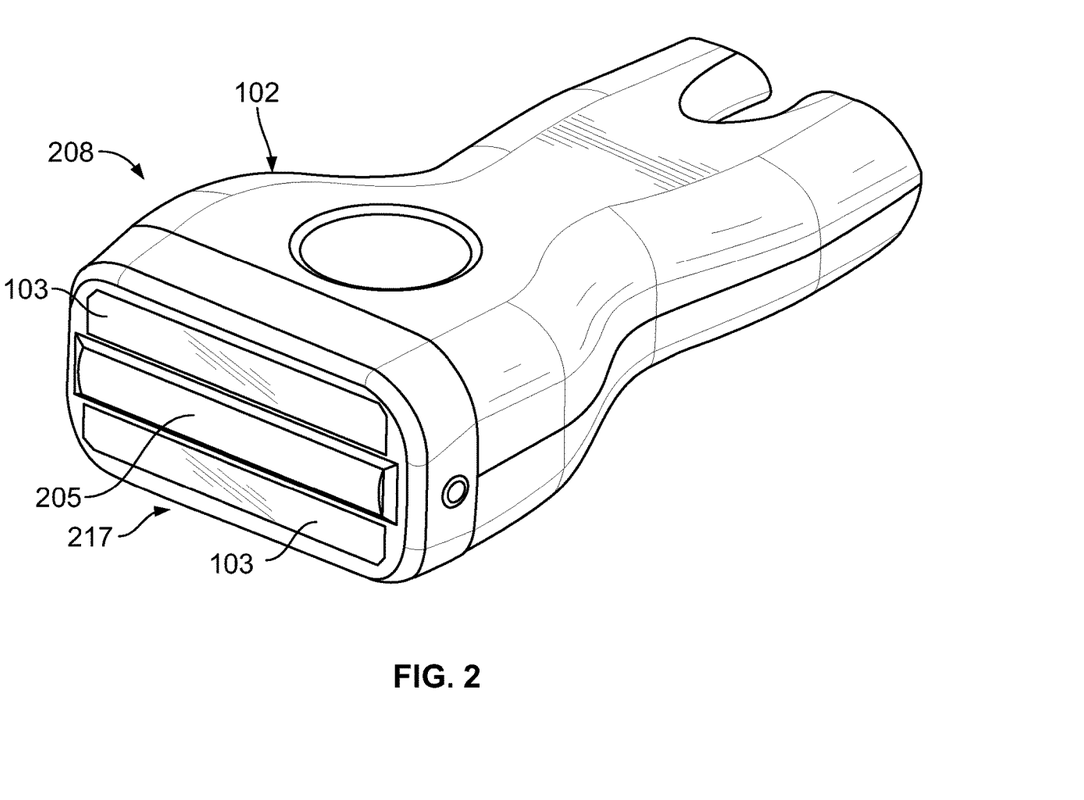
FIG. 2 shows a schematic orthogonal view of an embodiment of a probe that may be used in connection with the methods and other devices disclosed herein.

Turning now to FIG. 2, the probe 102 includes an ultrasound transducer covered by an acoustic lens 205. The probe 102 includes distal and proximal ends. A probe face 217 of the probe 102 is at the distal end 208. The probe 102 also includes one or more optical windows 103 through which the light is carried on light path 132 can be transmitted to the surface of a volume 160, for example, a three-dimensional volume. Specifically, the probe 102 may be placed in close proximity with organic tissue, phantom or other volume 160 that may have one or more inhomogeneities 161, 162, such as e.g., a tumor, within. An ultrasound gel (not shown) or other material may be used to improve acoustic coupling between the probe 102 and the surface of the volume 160 and/or to improve optical energy transfer.

Figure 3:
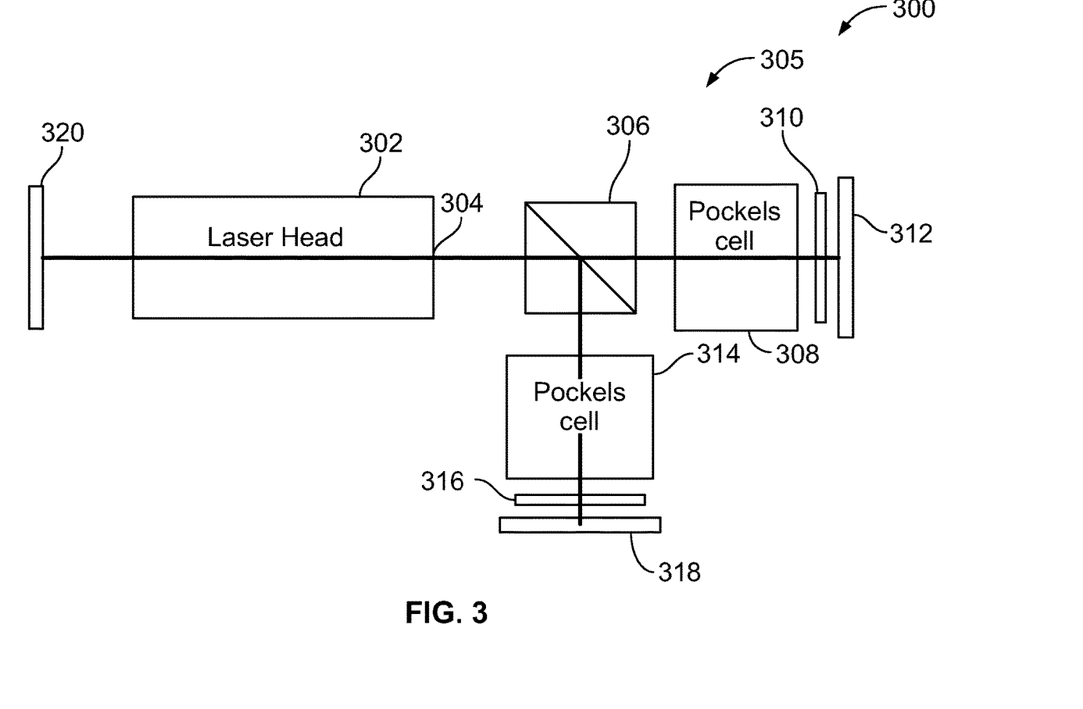
FIG. 3 shows a schematic view of a laser assembly used in connection with the methods and other devices disclosed herein.

Turning now to FIG. 3. FIG. 3 is a schematic view of an example embodiment of a laser assembly 300. In one embodiment, the laser assembly 300 of FIG. 3 is the laser assembly 129 of FIG. 1. The laser assembly 300 includes a laser pump chamber 302 that emits light from a laser cavity 304. The laser pump chamber 302 may include light generating materials, including Nd:YAG, or other lasing materials with lower temperatures than Alexandrite laser pumps. Specifically, Nd:YAG based material operates in a range between 10°-45° C. (50°-115° F.), while Alexandrite material operate more efficiently in a range between 80°-90° C. (175°-195° F.). By eliminating the Alexandrite laser pump from the laser assembly, a safer, more durable laser assembly is provided. In other embodiments, Nd:Vanadate, Nd:Glass, CrLiSAF, or the like may be used as the laser material.

The laser assembly 300 also includes polarization assembly 305. Polarized light waves are light waves where a wave's electrical field vibration happens in a single plane, such as an X-plane, Y-plane, or Z-plane. Through numerous techniques, including transmission, reflection, refraction, scattering, etc. light may be polarized. The polarization assembly 305 includes a polarizing beam splitter 306. In one embodiment, a polarizing beam splitter 306 receives emitted light and allows the light of a first polarization to transmit through the polarizing beam splitter 306 to provide the light polarized in a first plane, and also reflects the light of a second polarization normal, or perpendicular to the polarizing beam splitter 306, where the reflected light has the second different polarization. In this manner, the polarizing beam splitter utilizes transmission and reflection to form light of a same wavelength having different polarizations. In other embodiments, other methods may be used to transform light of the same wavelength into a first polarized light and a second polarized light having the same wavelength, but different polarizations.

The first polarized light that is transmitted through the polarizing beam splitter 306 is received by a first Pockels cell 308. Pockels cells function to rotate the polarization of the light passing therethrough when an electric field is applied across the crystal in the cell. The light then encounters the waveplate 310, which rotates the polarization without applied voltage. The first Pockels cell 308 and waveplate 310 are provided with a corresponding first reflection component 312. In one example, the first reflection component 312 is a mirror. The laser assembly 300 is designed so that only a single laser cavity 304 is provided. To accomplish, while having a first polarized light and second polarized light, the first polarized light is reflected off the first reflection component 312 back towards the polarizing beam splitter 306. The reflection and double pass through the waveplate results in the polarization being rotated, so the Pockels cell when activated rotates the first polarized light back to the polarization that transmits through the polarizing beam splitter 306. When the Pockels cell is not activated, the light reflects off the polarizing beam splitter 306, out of the system.

Meanwhile, the second polarized light that is reflected from the polarizing beam splitter 306 is received by a second Pockels cell 314 having a second waveplate 316. The second Pockels cell 314 is provided with a second reflection component 318. Again, the reflection results in the polarization to be rotated such that the second Pockels cell 314 when activated rotates the polarization back to the polarization that reflects off of the polarizing beam splitter 306, but transmits out of the system when not activated. As a result, the polarizing beam splitter 306 forms the first polarizing light and second polarizing light, and after receiving them from the first and second Pockels cells 308, 314 respectfully directs the first light and the second light back towards the laser cavity 304. In this manner, the polarizing beam splitter by splitting the light operates to pulse the light accordingly while keeping the same wavelength. So, the resultant first and second polarizing lights also provide pulses.

After the first polarized light and second polarized light are directed back towards and through the laser cavity 304, the resulting pulsed, dual polarized light is transmitted to an optical coupler 320, which reflects part of the light back into the cavity to seed more amplification, but transmits the rest to be used as the output. In one embodiment the light transmitted through the optical coupler goes to an optical parametric oscillator (OPO) that converts one of the pulsed, polarized laser beams (laser pump light) into two separate light outputs that have a frequency that adds up to the frequency of the laser pump light.

Figure 4:
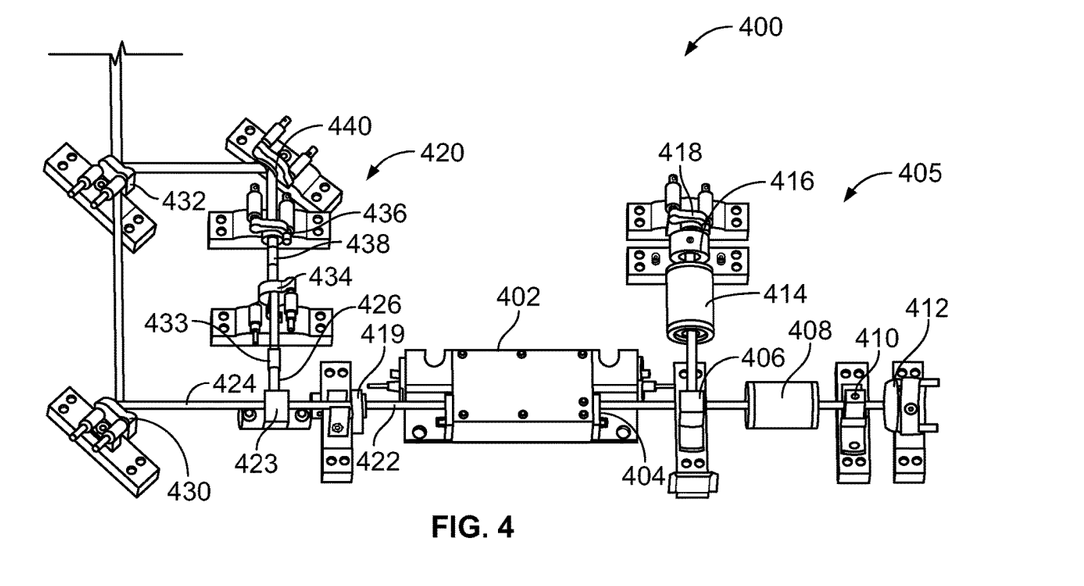
FIG. 4 is a top perspective view of a laser assembly used in connection with the method and other devices disclosed herein.

Turning now to FIG. 4, FIG. 4 illustrates a perspective view of a laser assembly 400. In one embodiment, the laser assembly 400 of FIG. 4 is the laser assembly 129 of FIG. 1 or laser assembly 300 of FIG. 3. The laser assembly 400 similar to laser assembly 300 includes a laser pump chamber 402 that emits light from a laser cavity 404, polarization assembly 405, a polarizing beam splitter 406, a first Pockels cell 408 having a waveplate 410 using a first reflection component 412, a second Pockels cell 414 having a high voltage second waveplate 416 with a second reflection component 418, and an optical coupler 419 In the view of laser assembly 400, the Optical Parametric Oscillator (OPO) 420 is illustrated in more detail.

In the embodiment of FIG. 4, the laser pump light 422 is illustrated being pumped from the laser pump chamber 402. The OPO 420 in the embodiment includes a beam splitter 423 that received the laser pump light 422 and splits the light into a first light 424, and second light 426 that both have the same wavelength and frequency. The first light 424 transmits through the beam splitter 423 to a first light reflective element 430 that reflects the first light to a beam transmission and reflector device 432 that allows the transmission of the first light with the wavelength and frequency of the laser pump light 422 to pass from and be emitted by the laser assembly 400. The second light 426 meanwhile transmits through a first light conversion element 433 that converts the wavelength of the first light from the first wavelength to a second wavelength. The second light 426 may then transmit through a first transmission device 434 to a second conversion element 438 to a second transmission device 436. These optics convert the second wavelength into a third wavelength which reflects off a reflection device 440 to the beam transmission and reflector device 432 that reflects the second light 426 with the third wavelength to emit from the laser assembly 400 along with the first light 424. In all, the optical coupler 420 converts the laser pump light to the wavelengths and frequencies desired for use. Specifically, while only a change in wavelength is provided by the embodiment of FIG. 4, in other embodiments, frequency changes, additional beam splitting, wavelength changes, and the like may be utilized.

Figure 5A:
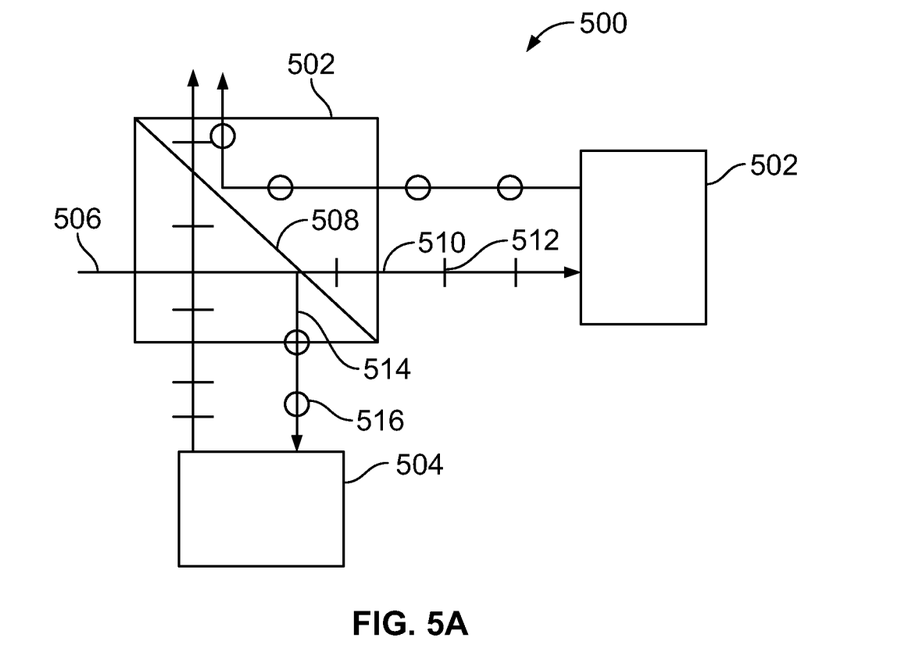
FIG. 5A is a schematic diagram of a polarizing beam splitter used in connection with the method and other devices disclosed herein.
Figure 5B:
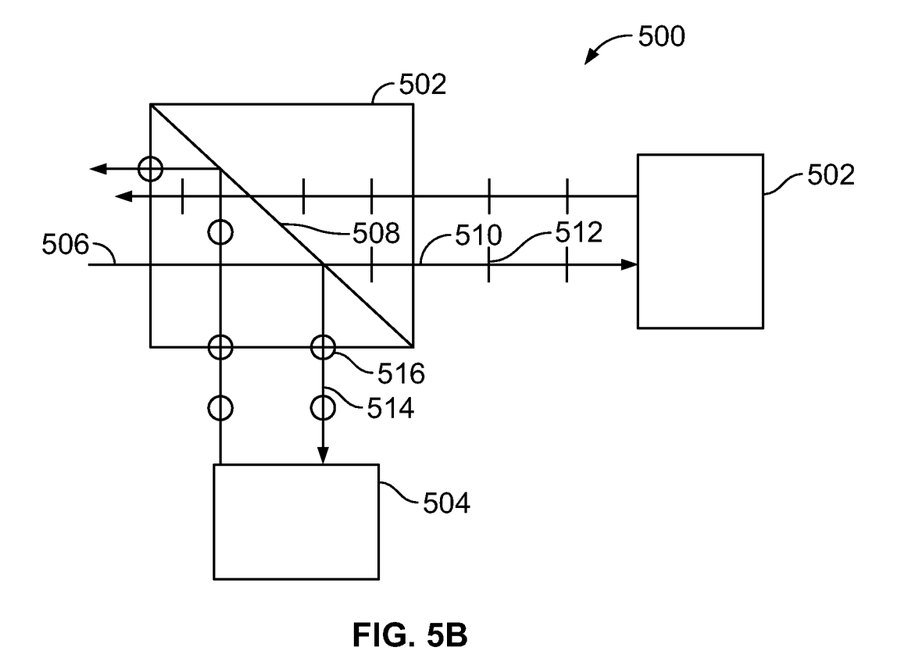
FIG. 5B is a schematic diagram of a polarizing beam splitter used in connection with the method and other devices disclosed herein.

Turning now to FIGS. 5A and 5B. FIG. 5A illustrates an example schematic diagram of a polarization assembly 500 with a polarizing beam splitter 501 with a first Pockels cell 502 and second Pockels cell 504 turned off, and not operating. FIG. 5B then illustrates the same polarizing beam splitter and first and second Pockels cells 502, 504 turned on, or operating. In one example, the first and second Pockels cells 502 and 504 are the first and second Pockels cells of FIG. 3 or 4, with each Pockels cell 502 and 504 including a waveplate and reflective element.

With reference to FIG. 5A, a pumped light 506 is pumped from a laser pump chamber having a determined frequency and wavelength. The pumped light 506 transmits to the beam splitting element 508 of the polarizing beam splitter causing the light to convert into a first light 510 with a first polarization 512, represented by dashes, that transmits through the polarizing beam splitter 501, and a second light 514 with a second polarization 516, represented by ovals, that reflects off the beam splitting element.

In the embodiment of FIG. 5A, when the first and second Pockels cells 502 and 504 are off, the reflection of the first light 510 causes the polarization of the first light 510 to convert from the first polarization to the second polarization. As a result, the first light reflects off the beam splitting element 508, exiting the beam splitter 501 in a direction away from the laser pump chamber. Similarly, the second light 514 also changes polarization by being reflected from the second Pockels cell 504 such that the second light transmits through the polarizing beam splitter 501, again, in a direction away from the laser pump chamber.

In the embodiment of FIG. 5B, when the first and second Pockels cells 502 and 504 are on, the reflection of the first and second Pockels cells function to maintain the polarization of the first light and second light through reflection. In this manner, the first light 510 has the first polarization 512 when leaving the first Pockels cell 502, resulting in the first light 510 transmitting through the beam splitting element 508 and back to the laser pump chamber. Meanwhile, the second light 514 has the second polarization 516 when leaving the second Pockels cell 504, resulting in the second light 514 reflecting off the beam splitting element 508 back towards the laser pump chamber. Consequently, a resultant pulsed laser pump light is formed from the first light 510 and second light 514 having different polarizations. The delay between the two pulses of light may be in a range between 50 µs to 400 µs, and in one example 200 µs. In this manner, the very low delay between alternating polarization allows for enhancing accuracy of readings in an optoacoustic environment, and eliminates the need for an extra laser pump that produces excess heat that can lead to wear, repair, and extra expense.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing example embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces, and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. A laser assembly comprising:
    a laser pump chamber that emits a first light through a laser cavity at a first wavelength; and
    a polarization assembly that receives the first light and converts the first light into a pulsed light that includes the first light at the first wavelength and a first polarization, and a second light at the first wavelength and a second polarization.

2. The laser assembly of claim 1, wherein the polarization assembly includes a polarizing beam splitter that converts the first light into the first light at the first wavelength and first polarization, and the second light at the first wavelength and the second polarization.

3. The laser assembly of claim 2, wherein the polarization assembly includes a first Pockels cell and a first reflective component that reflects the first light and a second Pockels cell and a second reflective component that reflects the second light.

4. The laser assembly of claim 2, wherein the polarization assembly includes a first waveplate and a second waveplate.

5. The laser assembly of claim 1, wherein the laser cavity is the only cavity of the laser that emits the first light.

6. The laser assembly of claim 1, further comprising an optical parametric oscillator that converts the pulsed light at the first wavelength into a first converted light at a second wavelength and a second converted light at a third wavelength.

7. The laser assembly of claim 6, wherein the first wavelength, second wavelength, and third wavelength are different wavelengths.

8. The laser assembly of claim 1, wherein the pulsed light pulses in a range between 50 microseconds and 400 microseconds.

9. An optoacoustic probe for optoacoustic imaging of a volume, the optoacoustic probe having a distal end operable to contact the volume and a proximal end, the optoacoustic probe comprising:
    a laser assembly configured to generate a pulsed light that includes a first light at a first wavelength and a first polarization, and a second light at the first wavelength and a second polarization along a light path to generate optoacoustic return signals when the light reacts with the volume;
    a transducer assembly including a transducer configured to receive the optoacoustic return signals and an acoustic lens provided over the transducer.

10. The optoacoustic probe of claim 9 wherein the laser assembly includes a polarizing beam splitter that receives light from a laser pump chamber and converts the light into the first light at the first wavelength and the first polarization and the second light at the first wavelength and the second polarization.

11. The optoacoustic probe of claim 10, wherein the laser assembly includes a first Pockels cell and first reflective component that reflects the first light back to the polarizing beam splitter, and a second Pockels cell and second reflective component that reflects the second light back to the polarizing beam splitter.

12. The optoacoustic probe of claim 10, wherein the laser assembly pump chamber has only one cavity.

13. The optoacoustic probe of claim 10, wherein the laser assembly pump chamber is made from only Nd:YAG based material.

14. The optoacoustic probe of claim 9, wherein the light is not emitted by a laser chamber pump having an Alexandrite based material.

15. The optoacoustic probe of claim 9 wherein the laser assembly includes an optical parametric oscillator that converts the pulsed light into a first converted light at a second wavelength and a second converted light at a third wavelength.

16. The optoacoustic probe of claim 9, wherein the pulsed light is pulsed in a range of between 50 microseconds and 400 microseconds between pulses.

17. An optoacoustic probe for optoacoustic imaging of a volume, the optoacoustic probe having a distal end operable to contact the volume and a proximal end, the optoacoustic probe comprising:
    a laser assembly configured to generate a pulsed light at less than 200 microseconds between pulses along a light path to generate optoacoustic return signals when the light reacts with the volume, the laser assembly including a polarization assembly that receives a first light and converts the first light into the pulsed light, the pulsed light including the first light at a first wavelength and a first polarization, and a second light at the first wavelength and a second polarization;
    a transducer assembly including a transducer configured to receive the optoacoustic return signals and an acoustic lens provided over the transducer.

18. The optoacoustic probe of claim 17 wherein the laser assembly includes a laser pump chamber that emits the first light at the first wavelength, and a polarizing beam splitter that converts the first light into a first converted light with the first polarization, and a second converted light at the second polarization that is opposite the first polarization.

19. The optoacoustic probe of claim 18, wherein the laser pump chamber is made from only Nd:YAG based material.

20. The optoacoustic probe of claim 17, wherein the laser assembly only has a single laser pump chamber.

* * * * *